United States Patent [19]

Kambara

[11] 4,404,964
[45] Sep. 20, 1983

[54] ENDOSCOPE OCULAR DEVICE

[75] Inventor: Koji Kambara, Sagamihara, Japan

[73] Assignee: Olympus Optical Co., Ltd., Tokyo, Japan

[21] Appl. No.: 204,897

[22] Filed: Nov. 7, 1980

[30] Foreign Application Priority Data

Nov. 15, 1979 [JP] Japan .............................. 54-148209

[51] Int. Cl.³ .............................................. A61B 1/00
[52] U.S. Cl. ......................................... 128/4; 354/62; 354/286
[58] Field of Search ................. 128/6, 4; 354/286, 62

[56] References Cited

U.S. PATENT DOCUMENTS

| | | |
|---|---|---|
| 3,823,411 | 7/1974 | Hasegawa et al. .................. 354/286 |
| 3,968,504 | 7/1976 | Komine ............................... 354/286 |
| 4,092,656 | 5/1978 | Lang et al. ........................... 354/286 |
| 4,130,358 | 12/1978 | Lang et al. ........................... 354/286 |
| 4,196,997 | 4/1980 | Ohmori et al. ....................... 354/286 |
| 4,247,190 | 1/1981 | Hashimoto et al. ................. 354/286 |

FOREIGN PATENT DOCUMENTS 2549380  5/1977  Fed. Rep. of Germany ...... 354/286

Primary Examiner—Kyle L. Howell
Assistant Examiner—Max F. Hindenburg
Attorney, Agent, or Firm—Frishauf, Holtz, Goodman & Woodward

[57] ABSTRACT

An endoscope ocular device comprises a hollow cylindrical housing and a return ring which is rotatably mounted on the housing, and rotated with a photographic camera fixed in place, whereby adjusting an ocular to a prescribed dioptric position, no matter how the ocular was previously disposed. A contact chamber is provided between the return ring and housing. Provided in the return ring is a first electrical contact, one end of which is exposed to the outer periphery of the return ring, and the other end of which projects into the contact chamber. Provided in the contact chamber is a second electrical contact which is removed from the first electrical contact when the photographic camera is taken off, and connected to the first electrical contact when the photographic camera is fixed in place, and is also connected to an electric power source. That end of the first electrical contact which is exposed to the outer periphery of the return ring is accessible and can be cleaned with water quickly and reliably. When the photographic camera is taken off the ocular device, the first electrical contact is disengaged from the second electrical contact. Therefore, the operator who happens to touch the exposed end of the first electrical contact is not subject to an electric shock.

5 Claims, 8 Drawing Figures

ENDOSCOPE OCULAR DEVICE

BACKGROUND OF THE INVENTION

This invention relates to an endoscope ocular device to be fitted with a photographic camera.

With an endoscope whose ocular section is fitted with a photographic camera, electrical contacts are generally provided on the oscular section in an exposed state. The electrical contacts are directly connected to an electric power source through the endoscope and are normally rendered alive. A person, who happens to touch the electrical contacts receives an electrical shock with possible danger. Therefore, the electrical contacts are provided in a cavity formed in an ocular section opening in a state unlikely to be touched by a person.

However, a chemical solution used to disinfect the endoscope ocular section tends to be carried into the cavity, presenting considerable difficulties in being wiped off. Further drawbacks experienced in the past are that the endoscope is sometimes left unused with the chemical solution still retained in the cavity, resulting in an electric shock to the operator by short circuiting or in damage to the ocular section; and the electrical contact formed in the cavity because of its hard accessibility for wiping, is subject to oxidation and chemical corrosion, giving rise to obstruction of electrical conduction.

It is accordingly an object of this invention to provide an endoscope ocular device which is so constructed that a person who happens to touch the ocular device stripped of a photographic camera is less exposed to an electric shock, and the electrical contacts are formed in that part of the surface of the ocular device which is easily accessible for wiping.

SUMMARY OF THE INVENTION

To attain the above-mentioned object, this invention provides an endoscope ocular device which comprises a hollow cylindrical housing penetrated by a concentric image guide from one end to its intermediate part, an ocular which is set opposite to the end face of the image guide in the housing in a state slidable axially of the housing, diopter-adjusting means concentrically provided in the housing in an axially movable but unrotatable state and operatively connected to the ocular lens, a return ring which is set in the housing in a rotatable but axially immovable state, and, in a first angular position, causes the ocular to take a desired dioptric position through the diopter-adjusting means, and, in a second angular position, disengages the ocular from the diopter-adjusting means, thereby allowing for the axial movement of the diopter-adjusting means, a contact chamber provided between the return ring and housing in a state extending circumferentially of the housing, a first contact formed in the return ring, one end of which is exposed to the outer peripheral wall of the return ring and the other end of which projects into the contact chamber, and a second contact which is set in the contact chamber, touches the other end of the first contact when the return ring is in the first angular position, is separated from the first contact when the return ring is in the second angular position and is further connected to an electric power source.

While the return ring is in the second angular position, the first contact remains electrically disengaged from the second contact, preventing the first contact from being supplied with electric power. The first contact is supplied with an electric power only when the return ring is rotated to the first angular position at the fitting of a photographic camera to the ocular device. Therefore, this invention offers the advantages that an operator who happens to touch the first contact before the fitting of the photographic camera to the ocular device is not subject to an electric shock; the first contact, one end of which is exposed to the outside from the outer peripheral wall of the return ring which is most accessible for wiping, can be wiped very easily; an endoscope dipped in a chemical solution for disinfection can be readily cleaned with water, preventing the electrical contact from being oxidized or chemically corroded, for example, by remnant water; and the electrical contact, if oxidized or chemically corroded, can be easily polished, enabling quick measures to be taken against the obstruction of electrical conduction.

This invention can be fully understoood from the following detailed description with reference to the accompanying drawings.

DETAILED DESCRIPTION

Figure 1:
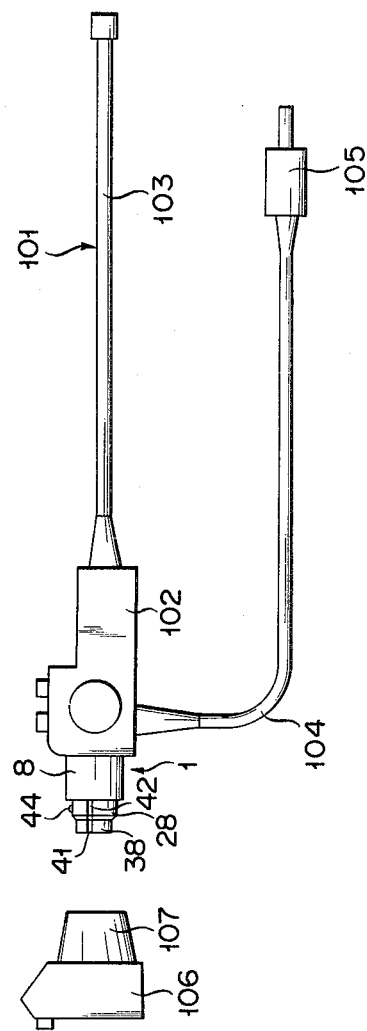
FIG. 1 is a lateral view of the whole of an endoscope fitted with an ocular device embodying this invention.

Referring to FIG. 1, an endoscope 101 comprises a control section 102, an insertion section 103, projecting from a distal end of the control section 102, and an umbilical cord 104 which extends from the control section 102 and whose free end is fitted with a connector 105. An ocular device 1 is provided at the proximal end of the control section 102. In the present invention the parts of the endoscope 101, other than the ocular device 1, have the same construction as those of the conventional type, description thereof being omitted.

Figure 2:
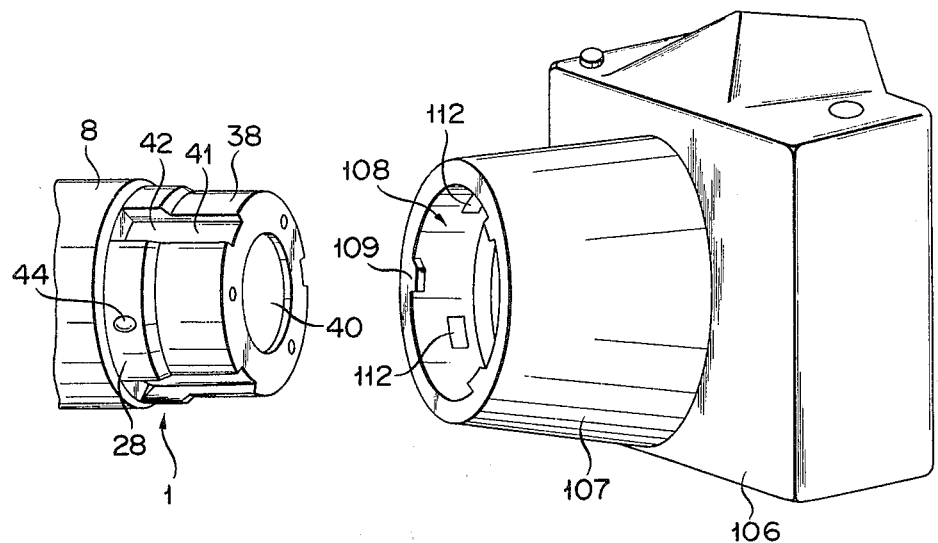
FIG. 2 shows an oblique view of the endoscope ocular device of FIG. 1 and a photographic camera to be connected to the ocular device.

As shown in FIG. 2, the ocular device 1 comprises the later described axially extending guide grooves 41 and engagement grooves 42. A photographic camera 106 has a hollow cylindrical fitting frame 107 whose bayonet section 108 is provided with bayonet pawls 109. When conducted through the guide grooves 41, the bayonet pawls 109 are engaged with the engagement grooves 42. When rotated thereafter in a prescribed direction, the photographic camera 106 is tightly connected to the ocular device 1.

Figure 3:
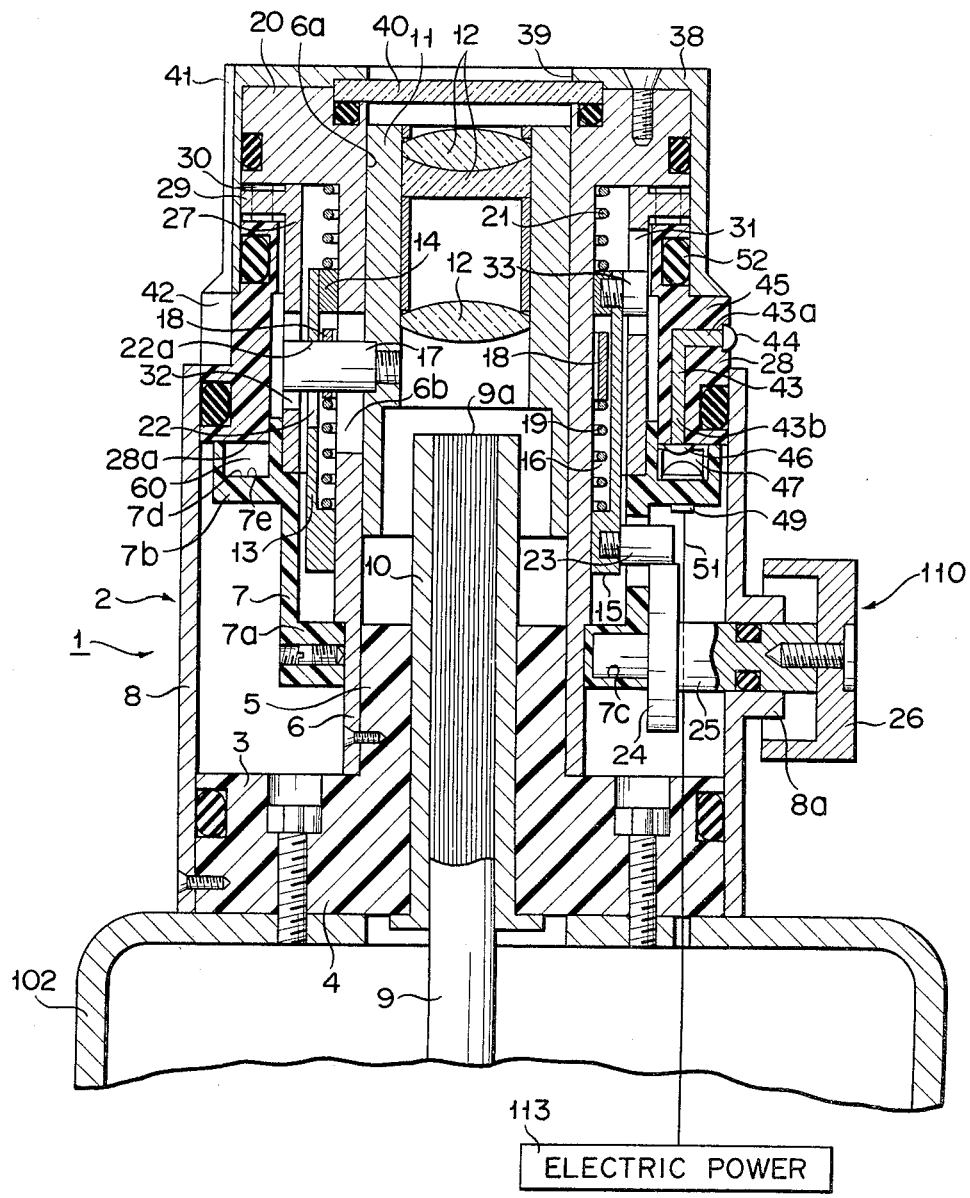
FIG. 3 is a longitudinal cross sectional view of the endoscope ocular device.

Description is now given of the construction of the ocular device 1 with reference to the longitudinal cross sectional view of FIG. 3. A fixing member 3 prepared from electrically nonconducting material such as plastic comprises a larger diameter cylindrical section 4 and an integral smaller diameter cylindrical section 5 extending concentrically from one end of the larger diameter cylindrical section 4. The fixing member 3 is tightly attached to the proximal end of the control section 102 at the other end of the larger diameter cylindrical section 4. One end of a central hollow cylindrical member 6 is securely fitted into the smaller diameter cylindrical section 5. The hollow cylindrical member 6 is enclosed in a hollow cylindrical support 7 formed of electrically nonconducting material such as plastic. The support 7 is concentrically fixed to the hollow cylindrical member 6 by a flange section 7a which is formed at that end of the support 7 which faces the fixing member 3 and radially extends toward the inner wall of the support 7. An image guide 9 which is formed of, for example, an optical fiber bundle and enclosed in a protective tube 10 concentrically extends through the fixing member 3. A distal end 9a of the image guide 9 extends beyond the smaller diameter cylindrical section 5.

A tubular lens frame 11 which faces the distal end 9a of the image guide 9 and holds an ocular 12 disposed concentrically with the image guide 9 is set in the distal end portion of a central hole 6a of the central hollow cylindrical member 6 in an axially slidable state.

A hollow cylindrical slider 13 surrounds the central hollow cylindrical member 6. A flange section 15 is provided at that end of the slider 13 which faces the fixing member 3. The flange section 15 radially extends toward the inner wall of the fixing member 3. The inner wall of the flange section 15 slidably abuts against the outer peripheral wall of the central hollow cylindrical member 6. Fixed, as described below, to the inner wall of the other end portion of the slider 13 is a sliding ring 14 whose inner diameter is equal to the outer diameter of the hollow cylindrical member 6. The slider 13 is axially guided along the surface of the central hollow cylindrical member by the flange section 15 and sliding ring 14.

The outer peripheral wall of the central hollow cylindrical member 6 and the portions of the inner peripheral wall of the slider 13 other than those facing the flange section 15 and sliding ring 14 jointly define an annular space 16. A ring member 18 is set in the space 16 to enclose the central hollow cylindrical member 6. The ring member 18 is penetrated by a diopter-adjusting pin 17 radially extending outward through an axially extending slot 6b formed in the wall of the central hollow cylindrical member 6.

Provided in the space 16 between the flange section 15 of the slider 13 and ring member 18 is a helical compression coil spring 19 which surrounds the central hollow cylindrical member 6 and urges the diopter-adjusting pin 17 to abut against the forward end 22a of an axial slit 22 formed in the slider 13. When the slider 13 is axially moved, the diopter-adjusting pin 17 is pushed while being pressed against the forward end 22a of the slit 22. Therefore, the lens frame 11 is shifted for the same distance and in the same direction as the slider 13.

The distal end of the central hollow cylindrical member 6 is provided with a larger diameter cylindrical section 20. A helical compression coil spring 21 is set between the inner end face of the larger diameter cylindrical section 20 and sliding ring 14 to surround the central hollow cylindrical member 6. The helical compression coil spring 21 normally urges the slider 13 toward the fixing member 5, thereby causing a cam pin 23 to abut against the lateral peripheral wall of an eccentric disc cam 24.

The central hollow cylindrical member 6 and slider 13 are surrounded by the later described rotatable diopter-adjusting cylindrical cam 27, the distal end of which is slidably pressed against the larger diameter cylindrical section 20 of the central hollow cylindrical member 6 and the proximal end of which is likewise slidably pressed against the distal end portion of the hollow cylindrical support 7. The cylindrical cam 27 is surrounded by a return ring 28 formed of electrically nonconducting material such as plastic. The rear end of the return ring 28 is slidably pressed against the forward end of the flange section 7b which is formed at the forward end of the hollow cylindrical support 7. The forward end of the return ring 28 is likewise slidably pressed against the inner end face of the larger diameter cylindrical section 20 of the central hollow cylindrical member 6.

One end portion of an outer tubular member 8 is securely fitted into the larger diameter cylindrical section 4 of the fixing member 3. The other end portion of the outer tubular member 8 extends to an intermediate part of the return ring 28. The fixing member 3, central hollow cylindrical member 6, hollow cylindrical support 7 and outer tubular member 8 jointly constitute a housing 2.

A diopter-adjusting mechanism 110 comprises a shaft 25, the eccentric disc cam 24 and the cam pin 23. The cam pin 23 radially projects outward from the flange section 15. One end of the shaft 25 is received in a radially extending hole 7c formed in the wall of the flange section 7a of the hollow cylindrical support 7, and projects from the outer tubular member 8 through a bearing 8a provided in the outer tubular member 8. The other end of the shaft 25 is provided with a knob 26. In the other tubular member 8, the eccentric disc cam 24 mounted on the shaft 25 has its lateral peripheral wall pressed against the cam pin 23.

The lift of the eccentric disc cam 24 varies with the extent of the rotation of the knob 26, causing the lens frame 11 to proceed or retract by means of the cam pin 23, slider 13 and diopter-adjusting pin 17, thereby controlling the diopter of the ocular 12.

A plurality of radially outward extending projections 29 are provided on the front end portion of the cylindrical cam 27 equidistantly in a circumferential direction. The projections 29 are engaged with axially extending slots or notches 30, causing the cylindrical cam 27 to be rotated through the same angle and in the same direction as the return ring 28.

A diopter-adjusting pin 33 projects radially outward from the front end portion of the slider 13. The pin 33 concurrently acts to fix the sliding ring 14 to the slider 13.

Figure 4:
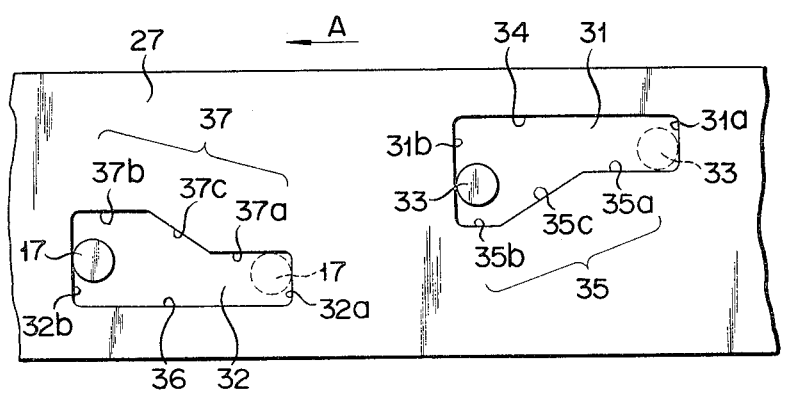
FIG. 4 is a developed view of a cylindrical cam cooperating with cam pins.

Referring to FIG. 4, the diopter-adjusting cylindrical cam 27 as openings 31, 32, respectively, penetrated by pins 33, 17. The opening 31 comprises a circumferentially extending edge 34 disposed on the front side of the cylindrical cam 27; a circumferentially extending cam face 35a close to the edge 34; a circumferentially extending cam face 35b more apart from the edge 34 than the cam face 35a; an inclined cam face 35c; and axially extending cam planes 31a, 31b connecting together the corresponding ends of both edges 34, 35 (the edge 35 being constituted by the cam faces 35a, 35b, 35c).

The opening 32 comprises an edge 36 disposed on the rear side of the cylindrical cam 27; an edge 37 formed on the front side of the cylindrical cam 27 (the edge 37 being constituted by a circumferentially extending cam faces 37a provided close to the edge 36, a cam face 37b set more apart from the edge 36 than the cam face 37a and an inclined cam face 37c connecting both cam faces 37a, 37b); and axially extending cam faces 32a, 32b connecting together the corresponding ends of both edges 36, 37.

When the diopter is adjusted to the observer's eye while the photographic camera 106 is not yet fitted to the ocular device 1, the pins 17, 33 are, respectively, drawn near to or contact the axially extending cam face 32b of the opening 32, and the axially extending cam face 31b of the opening 31.

Now let it be assumed with respect to FIG. 4 that the diopter-adjusting pins 17 and 33 are, respectively, set in a solid line position. When, under this condition, the cylindrical cam 27 is rotated in the direction of an arrow A (clockwise as viewed from the distal end of the ocular device 1), the pin 17 is guided by the inclined cam face 37c to take a broken line position contacting the circumferentially extending cam face 37a, causing the lens frame 11 to be so set as to bring the ocular 12 to a prescribed dioptric position, for example, a zero dioptric position.

When the diopter-adjusting pin 17 is retracted from an imaginary plane including the circumferentially extending cam face 37a, another diopter-adjusting pin 33 touches the inclined cam face 35c, which gradually guides the pin 33 toward the circumferentially extending cam surface 35a. During this period, the pin 33 pushes the slider 13 and pin 17. When the pin 33 contacts the circumferentially extending cam face 35a, the pin 17 touches the circumferentially extending cam face 37a, causing the ocular 12 to be reset in a prescribed dioptric position.

The cylindrical cam 27 is rotatable between a first angular position in which the pin 17 contacts the axial cam face 32a and a second angular position in which the pin 17 contacts the axial cam face 32b.

Reverting to FIG. 3, a mount body 38 is a hollow cylindrical member having a front end wall. The mount body 38 fixedly covers the larger diameter hollow cylindrical section 20 of the central hollow cylindrical member 6. The rear end of the mount body 38 encloses the front end of the return ring 28. The mount body 38 is fixed to the larger diameter hollow cylindrical section 20. A circular opening 39 concentric with the ocular 12 is formed in the front end wall of the mount body 38. A transparent glass cover 40 for closing the opening 39 is provided between the larger diameter hollow cylindrical section 20 and the front end wall of the mount body 38.

A plurality of axially extending guide grooves 41 engageable with the bayonet pawls 109 of the photographic camera 106 and extending along the whole length of the mount body 38 are formed in the outer peripheral wall of the hollow cylindrical mount body 38 equidistantly in the circumferential direction in the same number as the bayonet pawls 109. The engagement grooves 42 formed in the return ring 28 in the same number as the guide grooves 41 are aligned with the corresponding guide grooves 41 when the return ring 28 takes the second angular position. Under this condition, the bayonet pawls 109 are engaged with the corresponding guide grooves 41. When the photograpic camera 106 is pushed in, the bayonet pawls 109 are fitted into the engagement grooves 42. Thereafter, the photographic camera 106 is rotated clockwise as viewed from the front end of the ocular device 1. The return ring 28 takes the first angular position, causing the photographic camera 106 to be fixed to the ocular device 1.

Reverting to FIG. 3, first contacts 43 are provided in the return ring 28. These first contacts 43 are prepared from copper or any other electrically conductive material and used to supply electric power to the motor of the photographic camera 106 or to transmit various kinds of signals such as electric eye (EE) signals or synchronizing signals to the photographic camera 106. Each of the first contacts 43 is an L-shaped member comprising an arm 43a extending radially of the return ring 28 and an arm 43b extending axially of the return ring 28. The arm 43a has a free round-headed end 44, and the arm 43b has a free round-headed end 46. The round-headed end 44 projects about 0.3 mm from that portion of the outer peripheral wall 45 of the return ring 28 which is exposed to the atmosphere. Therefore, the accessible round-headed end 44 is easily cleaned with water after the endoscope is dipped in a chemical solution for disinfection, preventing the contact from being oxidized or chemically corroded by remnant water. If oxidized or chemically corroded, the round-headed end 44 can be readily polished, enabling proper measures to be quickly taken adjacent the possible obstruction of electric conduction.

An annular groove 7d defining an annular contact chamber 60 is formed in the flange section 7b of the hollow cylindrical support 7 in a state open to the front side of the flange section 7b.

The other round-headed end 46 of the arm 43a of each of the first contacts 43 projects into the contact chamber 60 from the rear end 28a of the return ring 28.

Figure 5:
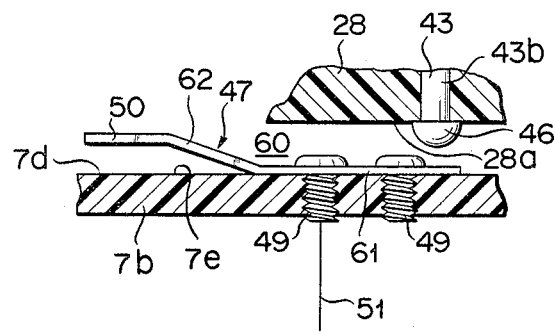
FIGS. 5 and 6 show the operation of a second contact according to one embodiment of the invention.
Figure 6:
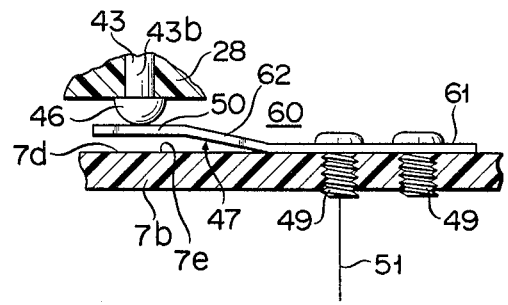

Referring to FIGS. 3, 5 and 6, a second contact 47 is provided in the annular contact chamber 60 in a state facing the round headed end 46 of the arm 43a of each of the first contacts 43. As shown in FIGS. 5 and 6, the second contact 47 is a plate member prepared from elastic electrically conductive material such as beryllium copper. The second plate contact 47 comprises a first flat section 61 (FIG. 5) which faces the round-headed end 46 of the first contact 43 when the return ring 28 takes the second angular position and is fixed by screws 49 to the bottom 7e of the groove 7d of the flange section 7b of the hollow cylindrical support 7 in a state set apart from the round headed end 46; a second flat section 50 which is separated toward the return ring 28 from the first flat section 61 in parallel therewith so as to be pressed against the round-headed end 46 of the arm 43a of the first contact 43 when the return ring 28 takes the first angular position; and an inclined section 62 connecting both first and second flat sections 61, 50 together. A lead 51 drawn out from one of the screws 49 passes through the fixing member 3, control section 102, and umbilical cord 104 to the connector 105, and is connected to an electric power source 113 provided in or outside of a light supply device (not shown).

When the return ring 28 is in the first angular position (FIG. 5), the round headed end 46 of the arm 43a of the first contact 43 is removed from the second contact 47, preventing the first contact 43 from being supplied with electric power. When the return ring 28 takes the second angular position, the round-headed end 46 of the arm 43a of the first contact 43 touches the inclined section 62 of the second contact 47 and finally rides on to the second flat section 50 while pressing the inclined section 62 toward the flange 7b (FIG. 6). As a result, the first contact 43 is supplied with electric power. Since, in this case, the fitting frame 107 of the photographic camera 106 encloses the return ring 28, the hands or any other part of the operator is not likely to touch the round-headed end 44 of the arm 43 of the first contact 43, thus protecting him from an electric shock. When the photographic camera 106 is fitted to the ocular device 1, the end 44 of the first contact 43 is connected to contacts 112 which are mounted on the inner wall of the fitting frame 107 for connection to circuits provided in the photographic camera 106 to drive the motor, or send forth the EE signal or synchronizing signal.

Figure 7:
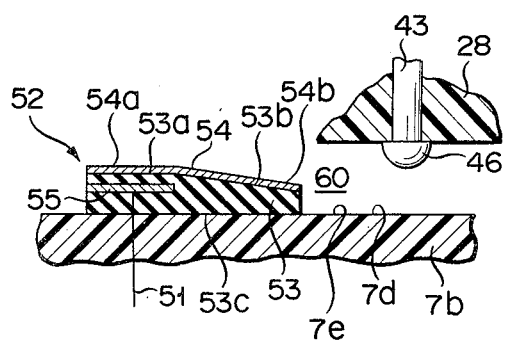
FIGS. 7 and 8 show the operation of a second contact according to another embodiment of the invention.
Figure 8:
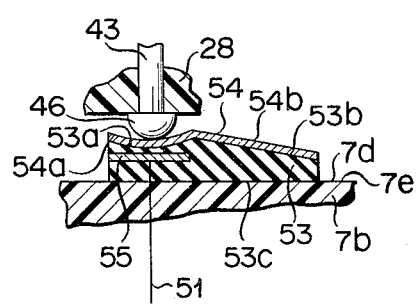

Description is now given with reference to FIGS. 7 and 8 of a second contact according to another embodiment of this invention. A second contact generally denoted by reference numeral 52 comprises a support member 53 which is prepared from electrically conductive rubber, and one plane 53c of which is fixed to the bottom 7e of an annular groove 7d formed in the flange section 7b of the hollow cylindrical support 7; a first contact strip 54 which is prepared from elastic electrically conductive material and set on the surface of the support member 53 facing the return ring 28; and a second contact strip 55 which is embedded in the support member 53 and connected to a lead 51.

That surface of the support 53 which faces the return ring 28 comprises a plane 53a parallel with the bottom 7e of the annular groove 7d formed in the flange section 7b, and an inclined plane 53b which is formed contiguously to the plane 53a, disposed nearer to the second angular position of the return ring 28, and is so inclined as to approach the annular groove 7d, as the return ring 28 is drawn near to the second angular position from the first angular position.

The first contact strip 54 comprises a flat plane 54a which is mounted on the plane 53a of the support 53 and set parallel with the bottom 7e of the annular groove 7d; and an inclined plane 54b fixed to the inclined plane 53b of the support 53. The inclined plane 54b of the first contact strip 54 is set at a sufficient height to be engaged with the round-headed end 46 of the arm 43a of the first contact 43.

The second contact strip 55 is embedded in the support 53 in a state disposed parallel with the flat plane 54a of the first contact strip 54 and defined within the region of the flat plane 54a.

The support 53 is prepared from elastic material such as pressure sensitive electrical conductive rubber which retains high electric resistance under a free condition, but, when depressed, decreases in electric resistance to allow for electric power supply. The first contact strip 54 is prepared from elastic electrically conductive material, such as beryllium copper. The second contact strip 55 is formed of electrically conductive material such as copper.

To give numerical data, the outer surface of the flat plane 54a of the first contact strip 54 is drawn about 0.4 mm nearer to the return ring 28 than the round-headed end 46 of the arm 43a of the first contact 43. The flat plane 54a is spaced about 0.6 mm from the second contact strip 55.

When the return ring 28 is in the first angular position, the round headed end 46 of the arm 43a of the first contact 43 is pressed against the flat plane 54a of the first contact strip 54. At this time, the flat plane 54a is bent in the arcuate form as illustrated in FIG. 8 and drawn close to the second contact strip 55. When that portion of the support 53 which faces the second contact strip 55 is thus depressed, the support 53 decreases in electric resistance, allowing electric power to be conducted from the lead 51 to the first contact strip 54 through the second contact strip 55. When the return ring 28 is in the second angular position, the round-headed end 46 of the arm 43a of the first contact 43 is displaced from the second contact 52 toward the second angular position of the return ring 28 to be completely separated from the second contact 52. As a result, the first contact 43 is not supplied with electric power.

The embodiment of FIGS. 7 and 8 is operated in a similar manner with a similar effect to that of FIGS. 5 and 6.

What is claimed is:

1. An endoscope ocular device which comprises:

a hollow cylindrical housing having two ends and which is concentrically penetrated by an image guide from one of said ends to an intermediate part of the housing;

an ocular mounted in the housing in a state facing said image guide and being movable axially of the housing;

rotatable diopter-adjusting means concentrically provided in the housing in a state movable axially of the housing and being operatively connected to the ocular;

a return ring operatively connected to the diopter-adjusting means, and which has an outer peripheral wall, the return ring being provided in the housing in a rotatable but axially immovable state such that the return ring, when taking a first angular position relative to the housing, causes the diopter-adjusting means to set the ocular in a prescribed dioptric positon, and, when taking a second angular position, causes the diopter-adjusting means to return to a position enabling axial movement;

a contact chamber disposed between the return ring and housing and extending circumferentially of the housing;

a source of electric power coupled to the housing;

a first electrical contact provided in the return ring and having two ends, one end of said first electrical contact being exposed to the outer periphery of the return ring, and the other end of said first contact projecting into the contact chamber; and a second electrical contact coupled to the electric power source and which is mounted in the contact chamber such that when the return ring is in the first angular position, the second electrical contact contacts the other end of the first electrical contact, and, when the return ring is in the second angular position, the second electrical contact is removed from the first electrical contact.

2. The endoscope ocular device according to claim 1, wherein said second electrical contact is an elastic electrically conductive strip which has a flat plane which extends circumferentially of the housing, and, when the return ring is in the first angular position, is pressed against the other end of the first electrical contact, and, when the return ring is in the second angular position, is removed from the other end of the first electrical contact; and which also has an inclined plane which is formed contiguously to the flat plane and extends therefrom toward the second angular position of the return ring and is progressively drawn near to the housing.

3. The endoscope ocular device according to claim 2, wherein the second electrical contact comprises a further flat plane made of electrically conductive material, and said further flat plane extending from the inclined plane to the second angular position of the return ring and also circumferentially of the housing, and being fixed in the housing and connected to the electric power source.

4. The endoscope ocular device according to claim 2, wherein said second electrical contact further comprises:
 a support made of pressuresensitive electrical conductive rubber, and said support having one plane which is shaped complementary to the contact strip and to which said contact strip is fixed, and an opposite plane which is fixed to the housing; and
 another contact strip which is embedded in the support in parallel with the flat plane of the first-mentioned contact strip and connected to the electric power source.

5. The endoscope ocular device according to any one of claims 1, 2, 3 or 4 wherein said contact chamber is defined by an annular groove formed in the housing.

* * * * *